(12) United States Patent
Carr et al.

(10) Patent No.: US 6,759,520 B1
(45) Date of Patent: Jul. 6, 2004

(54) CHIMERIC ANALGESIC PEPTIDES

(75) Inventors: Daniel B. Carr, Chestnut Hill, MA (US); Andrzej W. Lipkowski, Warsaw (PL); Richard Kream, Roslindale, MA (US); Aleksandra Misicka-Kesik, Piastow (PL)

(73) Assignee: The New England Medical Center Hospitals, Inc., Boston, MA (US)

( * ) Notice: Subject to any disclaimer, the term of this patent is extended or adjusted under 35 U.S.C. 154(b) by 0 days.

(21) Appl. No.: 09/428,692

(22) Filed: Oct. 28, 1999

(51) Int. Cl.[7] .......................... C07K 1/00; C07K 14/00; C07K 16/00; A61K 38/00; A01N 37/18
(52) U.S. Cl. .......................... 530/402; 530/300; 514/2
(58) Field of Search .......................... 514/2; 530/302, 530/300, 329, 330, 327, 402

(56) References Cited

U.S. PATENT DOCUMENTS

| 5,891,842 A | | 4/1999 | Kream |
| 6,063,758 A | * | 5/2000 | Lappi et al. |
| 6,310,072 B1 | * | 10/2001 | Smith et al. |

OTHER PUBLICATIONS

Watson et al. (Eur. J. Pharmacol. 87(1) :77–84, 1983.*
Cavagnero S., et al. Life Sci. 49(7):498–503, 1991.*
Lei et al., "Opioid an neurokinin activities of substance P fragments and their analogs", Eur. J. Pharmacol., 193(2):209–215, 1991.
Sizheng et al., "Opioid and neurokinin activities of substance P fragments and their analogs", Eur. J. Pharmacology, 193: 209–215, 1991.
Lipkowski et al., "An approach to the self regulatory mechanism of substance P actions: II. Biological activity of new synthetic peptide analogs related both to enkephalin and substance P", Life Sciences, 33(Sup. I): 141–144, 1983.
Foran et al., "Inhibition of Morphine Tolerance Development by a Substance P–Opioid Peptide chimera", J. Pharmacol. Exp. Ther., 295(3): 1142–1148, 2000.
Maszczynska et al., "Alternative forms of interaction of substance P and opioids in nociceptive transmission", Letters in Peptide Science, 5: 395–398, 1998.
Foran et al., "A substance P–opioid chimeric peptide as a unique nontolerance–forming analgesic", Proc. Natl. Acad. Sci., 97: 7621–7626, 2000.
Lipkowski et al., "Opioid Peptide Analogues: Reconsideration as a Potentially New Generation of Analgesics", Polish J. Chem., 68: 907–912, 1994.
Misterek et al., "Spinal co–administration of peptide substance P antagonist increases antinociceptive effect of the opioid peptide biphalin", Life Sciences, 54(14): 939–944, 1994.

Foran et al., "Chimeric peptide for the treatment of acute and chronic pain", Anesthesiology.
(Hagerstown), vol. 91, No. 3A, 1999, p. A944 XP000996135 Annual Meeting of the American Society of Anesthesiologists; Dallas, Texas, USA; Oct. 9–13, 1999 ISSN: 0003–3022.
Langel et al., "Design of chimeric peptide ligands to galanin receptors an substance P receptors", International Journal of peptide and protein research, DK, Munksgaard, Copenhagen, 39(6): 516–522, 1992.
Patent Abstracts of Japan, vol. 1999, No. 8, Jun. 30, 1999 & JP 11060598 A (Asashi Glass Co LTD), Mar. 2, 1999 abstract, p. 3, Formula 1(A).
Foran S., "Characterization of Novel Chimeric Analgesic Peptides", Ph.D. Dissertation, Tufts University, Sackler School of Graduate Biomedical Sciences, Sep. 2000.
Lipkowski et al., "Peptides as receptor selectivity modulators of opiate pharmacophores", J. Med. Chem., 29: 1222–1225, 1986.
Lipkowski et al., "Benzomorphan alkaloids, natural peptidomimetics of opioid peptide pharmacophores", Lett. Peptide Res., 2: 177–181, 1995.
Lipkowski et al., "Biological activities of a peptide containing both casomorphin–like and substance P antagonist structural characteristics", in Casomorphins and related peptides. Recent developments, V. Brantl, H. Teschemacher, eds, VCH, Weinheim, pp. 113–118, 1994.
Carr, et al., Neural Blockade in Clinical Anesthesia and Management of Pain, Third Ed., pp. 915–983 (1998).
Hylden, et al., Eur.J. Pharmacol., 86: 95–98 and J. Pharmacol. Exp. Ther. 226: 398–404 (1983).
Kream, et al., Proc. Nat'l. Acad. Sci. USA 90, 3564–3568 (1993).
Lipkowski, et al., Neuropeptides: Peptide and Nonpeptide Analogs, Gutte, ed., Academic Press pp. 287–320 (1995).
Maszczynska, et al., Analgesia, Dual Functional Interactions of Substance P and Opioids in Nociceptive Transmission: Review and Reconciliation, vol. 3, pp. 259–268 (1998).
Schiller, et al., J. Med. Chem. 36: 3182–3187 (1993).
Silbert, et al., Agents and Actions, vol. 33, pp. 382–387, Analgesic Activity of a Novel Bivalent Opioid Peptide Compared to Morphine Via Different Routes of Administration (1991).
Silbert, et al., Prog. Clin. Biol. Res. 328: 485–488 (1990).
Ward, J. Med. Chem. 33: 1848–1851 (1990).
Zadina, et al., Life Sci., 55: 461–466 (1994).

* cited by examiner

Primary Examiner—Gary Kunz
Assistant Examiner—Robert Landsman
(74) Attorney, Agent, or Firm—Brenda Herschbach Jarrell; Nadege M. Lagneau; Choate, Hall & Stewart

(57) ABSTRACT

The present invention provides a novel chimeric peptide containing an opioid peptide moiety and a nociceptive peptide moiety for producing analgesia.

29 Claims, 11 Drawing Sheets

CHIMERIC ANALGESIC PEPTIDES

FIELD OF THE INVENTION

The present invention relates generally to methods and compositions for the treatment of pain. More specifically, the present invention relates to novel chimeric peptides for the treatment of pain.

BACKGROUND OF THE INVENTION

Two million people in the United States suffer from chronic pain. Pain is caused by a highly complex perception of an aversive or unpleasant sensation. The sensation of pain begins with noxious stimulation of free nerve endings, which leads to activation of different types of nociceptive afferent fibers. These fibers include Aδ fibers and C fibers. Aδ fibers are small diameter, thinly myelinated fibers that transmit sharp, prickling pain. C fibers are unmyelinated and conduct more slowly and transmit dull, aching pain. Repeated stimulation of pain fibers can lead to hyperalgesia, or a lowering of the threshold for activation of nociceptors.

Primary afferent fibers Aδ or C from the damaged periphery synapse release a variety of chemical mediators. These mediators include glutamate and substance P ("SP"), a nociceptive peptide. SP has long been recognized and identified as a neurotransmitter intimately associated with the transfer of painful or nociceptive stimuli from peripheral receptive fields into the CNS. This neuropeptide is involved in pain signaling and the maintenance of the chronic pain state. SP is the prototypic member of a family of related peptides named tachykinins, all of which were initially characterized by contractile activity on isolated smooth muscle preparations. SP is also found in the brain, spinal cord, spinal ganglia, and intestine of all vertebrates, including man.

SP is present in small-diameter sensory fibers that mediate nociceptive inputs in the spinal cord, and it specifically excites nociceptive neurons in this region. SP is released in the spinal cord in vivo, upon activation of nociceptive primary sensory fibers. Direct application of microgram doses of SP into the lumbar spinal subarachnoid produces hyperalgesia, i.e., an increased sensitivity to pain. The release of SP can be blocked by administration of morphine and opioid peptides in vivo and in vitro. For example, intrathecal administration of morphine blocks the hyperalgesic effects of exogenously administered SP. See, Hyden and Wilcox, Eur. J. Pharmacol., 86: 95–98 (1983); and J. Pharmacol. Exp. Ther. 226: 398–404 (1983).

While opioids can be effective for the treatment of chronic pain, they frequently have side effects, including respiratory depression, urinary retention, nausea and vomiting, pruritis, and sedation. Moreover, repeated daily administration of opioids eventually produces tolerance, whereby the dose of the drug must be increased in order to maintain adequate analgesia, and may also initiate physical dependence. If tolerance develops and the level of opioids is insufficient, withdrawal symptoms such as diarrhea, sweating, tremors, anxiety, and fever may result. These concerns have prompted a search for new analgesics with limited side effects and that show decreased susceptibility to tolerance.

SUMMARY OF THE INVENTION

The present invention provides a novel chimeric peptide having an opioid moiety that binds to an opioid receptor and a nociceptive moiety that binds to a nociceptive receptor, such as $NK_1$. The opioid moiety may be directed to any of the opioid receptor types, including the μ, δ, or κ receptor For example, the chimeric peptide can include an μ-receptor binding opioid moiety and an $NK_1$-binding SP moiety. In one embodiment this chimeric peptide has the sequence: Tyr-Pro-Phe-Phe-Gly-Leu-Met-$NH_2$ (SEQ ID NO:42).

The chimeric peptides may be designed to have a plurality of SP moieties and a plurality of opioid moieties. The plurality of opioid moieties may be directed to the same receptor type, or, alternatively, the plurality of opioid moieties may be directed to different opioid receptor types.

The invention provides pharmaceutical compositions including chimeric peptides and a pharmaceutically acceptable carrier useful for the treatment of pain.

The invention also provides a method of treating pain by administering the chimeric peptide capable of binding to both an opioid receptor and the $NK_1$ receptor admixed with a pharmaceutically acceptable carrier, such as pharmaceutical sterile saline. The peptide may be administered intrathecally (IT), intracerebrovertricularlly (ICV) or systemically, for example, intraperitoneally (IP). Solubility of the chimeric peptides may be enhanced by admixture with a solubilizing agent, for example, cyclodextran. In a alternative embodiment, a chimeric peptide is administered in conjunction with one or more non-chimeric opioid drugs.

Among the advantages of the invention is that the chimeric peptides produce effective analgesia yet inhibit the development of tolerance.

The details of one or more embodiments of the invention are set forth in the accompanying description below. Although any methods and materials similar or equivalent to those described herein can be used in the practice or testing of the present invention, the preferred methods and materials are now described. Other features, objects, and advantages of the invention will be apparent from the description and from the claims. In the specification and the appended claims, the singular forms include plural referents unless the context clearly dictates otherwise. Unless defined otherwise, all technical and scientific terms used herein have the same meaning as commonly understood by one of ordinary skill in the art to which this invention belongs. Unless expressly stated otherwise, the techniques employed or contemplated herein are standard methodologies well known to one of ordinary skill in the art. The examples of embodiments are for illustration purposes only. All patents and publications cited in this specification are incorporated herein by reference.

DETAILED DESCRIPTION OF THE INVENTION

Figure 1:
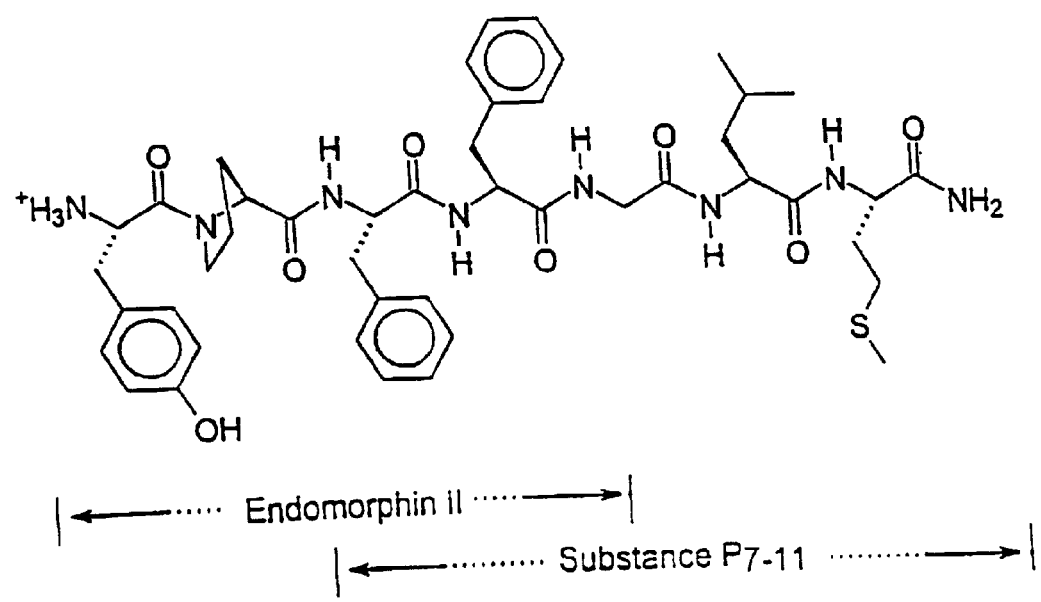
FIG. 1 is a schematic representation of the chimeric peptide ESP7.

The present invention provides a chimeric peptide having an opioid receptor binding moiety and a nociceptive receptor binding moiety (e.g., Substance P). The chimeric peptide molecules may be designed to bind to any of the opioid receptors known to be involved in pain mediation. See review in Lipkowski and Carr, *Peptides: Synthesis, Structures, and Applications,* Gutte, ed., Academic Press pp. 287–320 (1995), incorporated herein by reference. While the opioid peptides frequently exhibit some cross reactivity with the different receptor types, they can be generally characterized by the degree of affinity for a particular receptor type. These receptors include the $\mu$ receptor, the $\delta$ receptor and the $\kappa$ receptor.

The separate moieties may be chemically synthesized and purified or isolated from natural sources and then chemically cross-linked to form the chimeric peptide. Alternatively, the chimera can be chemically synthesized as one molecule. In another embodiment, chimeric peptides are produced by recombinant DNA techniques and isolated from cells or tissue sources by an appropriate purification scheme using standard protein purification techniques. The invention also relates to derivatives, fragments, homologs, analogs and variants of these peptides.

Chemical Synthesis

Chimeric peptides, and individual moieties or analogs and derivatives thereof, can be chemically synthesized. A variety of protein synthesis methods are common in the art, including synthesis using a peptide synthesizer. See, e.g., *Peptide Chemistry, A Practical Textbook,* Bodasnsky, Ed. Springer-Verlag, 1988; Merrifield, *Science* 232: 241–247 (1986); Barany, et al, *Intl. J. Peptide Protein Res.* 30: 705–739 (1987); Kent, *Ann. Rev. Biochem.* 57:957–989 (1988), and Kaiser, et al, *Science* 243: 187–198 (1989). The peptides are purified so that they are substantially free of chemical precursors or other chemicals using standard peptide purification techniques. The language "substantially free of chemical precursors or other chemicals" includes preparations of peptide in which the peptide is separated from chemical precursors or other chemicals that are involved in the synthesis of the peptide. In one embodiment, the language "substantially free of chemical precursors or other chemicals" includes preparations of peptide having less than about 30% (by dry weight) of chemical precursors or non-peptide chemicals, more preferably less than about 20% chemical precursors or non-peptide chemicals, still more preferably less than about 10% chemical precursors or non-peptide chemicals, and most preferably less than about 5% chemical precursors or non-peptide chemicals.

Chemical synthesis of peptides facilitates the incorporation of modified or unnatural amino acids, including D-amino acids and other small organic molecules. Replacement of one or more L-amino acids in a peptide with the corresponding D-amino acid isoforms can be used to increase the resistance of peptides to enzymatic hydrolysis, and to enhance one or more properties of biologically active peptides, i.e., receptor binding, functional potency or duration of action. See, e.g., Doherty, et al., 1993. *J. Med. Chem.* 36: 2585–2594; Kirby, et al., 1993. *J. Med. Chem.* 36:3802–3808; Morita, et al., 1994. *FEBS Lett.* 353: 84–88; Wang, et al., 1993. *Int. J. Pept. Protein Res.* 42: 392–399; Fauchere and Thiunieau, 1992.*Adv. Drug Res.* 23: 127–159.

Introduction of covalent cross-links into a peptide sequence can conformationally and topographically constrain the peptide backbone. This strategy can be used to develop peptide analogs of the chimeric peptides with increased potency, selectivity and stability. Because the conformational entropy of a cyclic peptide is lower than its linear counterpart, adoption of a specific conformation may occur with a smaller decrease in entropy for a cyclic analog than for an acyclic analog, thereby making the free energy for binding more favorable. Macrocyclization is often accomplished by forming an amide bond between the peptide N- and C-termini, between a side chain and the N- or C-terminus [e.g., with $K_3Fe(CN)_6$ at pH 8.5] (Samson et al., *Endocrinology,* 137: 5182–5185 (1996)), or between two amino acid side chains. See, e.g., DeGrado, *Adv Protein Chem,* 39: 51–124 (1988). Disulfide bridges are also introduced into linear sequences to reduce their flexibility. See, e.g., Rose, et al., *Adv Protein Chem,* 37: 1–109 (1985); Mosberg et al., *Biochem Biophys Res Commun,* 106: 505–512 (1982). Furthermore, the replacement of cysteine residues with penicillamine (Pen, 3-mercapto-(D) valine) has been used to increase the selectivity of some opioid-receptor interactions. Lipkowski and Carr, *Peptides: Synthesis, Structures, and Applications,* Gutte, ed., Academic Press pp. 287–320 (1995).

A number of other methods have been used successfully to introduce conformational constraints into peptide sequences in order to improve their potency, receptor selectivity and biological half-life. These include the use of (i) $C_\alpha$-methylamino acids (see, e.g., Rose, et al., *Adv Protein Chem,* 37: 1–109 (1985); Prasad and Balaram, *CRC Crit Rev Biochem,* 16: 307–348 (1984)); (ii) $N_\alpha$-methylamino acids (see, e.g., Aubry, et al., *Int J Pept Protein Res,* 18: 195–202 (1981); Manavalan and Momany, *Biopolymers,* 19: 1943–1973 (1980)); and (iii) $\alpha,\beta$-unsaturated amino acids (see, e.g., Bach and Gierasch, *Biopolymers,* 25: 5175-S 192 (1986); Singh, et al., *Biopolymers,* 26: 819–829 (1987)). These and many other amino acid analogs are commercially available, or can be easily prepared. Additionally, replacement of the C-terminal acid with an amide can be used to enhance the solubility and clearance of a peptide.

Recombinant Peptides

Alternatively, the peptides may be obtained by methods well-known in the art for recombinant peptide expression and purification. A DNA molecule encoding a chimeric peptide can be generated. The DNA sequence is deduced from the protein sequence based on known codon usage. See, e.g., Old and Primrose, *Principles of Gene Manipulation* $3^{rd}$ ed., Blackwell Scientific Publications, 1985; Wada et al., *Nucleic Acids Res.* 20: 2111–2118(1992). Preferably, the DNA molecule includes additional sequence, e.g., recognition sites for restriction enzymes which facilitate its cloning into a suitable cloning vector, such as a plasmid. The invention provides the nucleic acids comprising the coding regions, non-coding regions, or both, either alone or cloned in a recombinant vector, as well as oligonucleotides and related primer and primer pairs corresponding thereto. Nucleic acids may be DNA, RNA, or a combination thereof. Vectors of the invention may be expression vectors. Nucleic acids encoding chimeric peptides may be obtained by any method known within the art (e.g., by PCR amplification using synthetic primers hybridizable to the 3'- and 5'-termini of the sequence and/or by cloning from a cDNA or genomic library using an oligonucleotide sequence specific for the given gene sequence, or the like). Nucleic acids can also be generated by chemical synthesis.

The invention relates to nucleic acids hybridizable -or complementary- to the nucleic acids encoding the chimeric peptides. In particular the invention provides the inverse complement to nucleic acids hybridizable to the encoding nucleic acids (i.e., the inverse complement of a nucleic acid strand has the complementary sequence running in reverse orientation to the strand so that the inverse complement would hybridize with few or no mismatches to the nucleic acid strand). Nucleic acid molecules encoding derivatives and analogs of a chimeric peptide, or antisense nucleic acids to the same are additionally provided.

Any of the methodologies known within the relevant art regarding the insertion of nucleic acid fragments into a vector may be used to construct expression vectors that contain a chimeric gene comprised of the appropriate transcriptional/translational control signals and peptide-coding sequences. Promoter/enhancer sequences within expression vectors may use plant, animal, insect, or fungus regulatory sequences, as provided in the invention.

A host cell can be any prokaryotic or eukaryotic cell. For example, the peptide can be expressed in bacterial cells such as *E. coli*, insect cells, fungi or mammalian cells (such as Chinese hamster ovary cells (CHO) or COS cells). Other suitable host cells are known to those skilled in the art. In one embodiment, a nucleic acid encoding the peptide is expressed in mammalian cells using a mammalian expression vector. Examples of mammalian expression vectors include pCDM8 (Seed (1987) *Nature* 329:840) and pMT2PC (Kaufman et al. (1987) *EMBO J* 6: 187–195). Furthermore, transgenic animals containing nucleic acids that encode a chimeric peptide may also be used to express peptides of the invention.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (*Molecular Cloning: A Laboratory Manual.* 2nd ed., Cold Spring Harbor Laboratory, Cold Spring Harbor Laboratory Press, Cold Spring Harbor, N.Y., 1989), and other laboratory manuals.

More commonly, the host cells, can be used to produce (ie., over-express) peptide in culture. Accordingly, the invention further provides methods for producing the peptide using the host cells of the invention. In one embodiment, the method comprises culturing the host cell of invention (into which a recombinant expression vector encoding the peptide has been introduced) in a suitable medium such that peptide is produced. The method further involves isolating peptide from the medium or the host cell. Ausubel et al., (Eds). In: *Current Protocols in Molecular Biology.* J. Wiley and Sons, New York, N.Y. 1998.

An "isolated" or "purified" recombinant peptide or biologically active portion thereof is substantially free of cellular material or other contaminating proteins from the cell or tissue source from which the peptide of interest is derived. The language "substantially free of cellular material" includes preparations in which the peptide is separated from cellular components of the cells from which it is isolated or recombinantly produced. In one embodiment, the language "substantially free of cellular material" includes preparations of peptide having less than about 30% (by dry weight) of peptide other than the desired peptide (also referred to herein as a "contaminating protein"), more preferably less than about 20% of contaminating protein, still more preferably less than about 10% of contaminating protein, and most preferably less than about 5% contaminating protein. When the peptide or biologically active portion thereof is recombinantly produced, it is also preferably substantially free of culture medium, ie., culture medium represents less than about 20%, more preferably less than about 10%, and most preferably less than about 5% of the volume of the peptide preparation.

Cells engineered to over-express a chimeric peptide can also be introduced in vivo for therapeutic purposes by any method known in the art, including, but not limited to, implantation or transplantation of cells into a host subject, wherein the cells may be "baked" or encapsulated prior to implantation. Cells may be screened prior to implantation for various characteristics including, but not limited to, the level of peptide secreted, stability of expression, and the like.

Production of Derivatives and Analogs

The present invention also pertains to variants of the peptides that function as either agonists (mimetics) or as antagonists. Variants of a parent peptides can be generated by mutagenesis, e.g., discrete point mutation. An agonist of a parent peptide can retain substantially the same, or a subset of, the biological activities of the naturally occurring form of the parent peptide. An antagonist of the peptide can inhibit one or more of the activities of the naturally occurring form of the parent peptide by, for example, competitively binding to the receptor. Thus, specific biological effects can be elicited by treatment with a variant with a limited function. In one embodiment, treatment of a subject with a variant having a subset of the biological activities of the naturally occurring form of the peptide has fewer side effects in a subject relative to treatment with the naturally occurring form of the parent peptide.

Preferably, the analog, variant, or derivative peptides are functionally active. As utilized herein, the term "functionally active" refers to species displaying one or more known functional attributes of a full-length peptide. "Variant" refers to a polynucleotide or polypeptide differing from the polynucleotide or polypeptide of the present invention, but retaining essential properties thereof. Generally, variants are overall closely similar, and in many regions, identical to the polynucleotide or polypeptide of the present invention. The variants may contain alterations in the coding regions, non-coding regions, or both.

Variants of the peptides that function as either agonists (mimetics) or as antagonists can be identified by screening combinatorial libraries of mutants of the parent peptide for peptide agonist or antagonist activity. In one embodiment, a variegated library of variants is generated by combinatorial mutagenesis at the nucleic acid level and is encoded by a variegated gene library. A variegated library of variants can be produced by, for example, enzymatically ligating a mixture of synthetic oligonucleotides into gene sequences such that a degenerate set of potential sequences is expressible as individual peptides, or alternatively, as a set of larger fusion proteins (e.g., for phage display) containing the set of sequences therein. There are a variety of methods which can be used to produce libraries of potential variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential sequences. Methods for synthesizing degenerate oligonucleotides are known in the art (see, e.g., Narang (1983) *Tetrahedron* 39:3; Itakura et al. (1984) *Annu Rev Biochem* 53:323; Itakura et al. (1984) *Science* 198:1056; Ike et al. (1983) *Nucl Acid Res* 11:477.

Derivatives and analogs of the chimeric peptides or individual moieties can be produced by various methods known within the art. For example, the polypeptide sequences may be modified by any of numerous methods known within the art. See e.g., Sambrook, et al., 1990. *Molecular Cloning: A Laboratory Manual, 2nd ed.,* (Cold Spring Harbor Laboratory Press; Cold Spring Harbor, N.Y.). Manipulations can include by glycosylation, acetylation, phosphorylation, amidation, derivatization by known protecting/blocking groups, linkage to an antibody molecule or other cellular ligand, and the like. Any of the numerous chemical modification methodologies known within the art may be utilized including, but not limited to, specific chemical cleavage by cyanogen bromide, trypsin, chymotrypsin, papain, V8 protease, $NaBH_4$, acetylation, formylation, oxidation, reduction, metabolic synthesis in the presence of tunicamycin, etc. In one embodiment, the peptide is modified by the incorporation of a heterofunctional reagent, wherein such heterofunctional reagents may be used to connect the opioid moiety to the nociceptive moiety.

Derivatives, fragments, and analogs provided herein are defined as sequences of at least 6 (contiguous) nucleic acids or at least 4 (contiguous) amino acids, a length sufficient to allow for specific hybridization in the case of nucleic acids or for specific recognition of an epitope in the case of amino acids, respectively. Fragments are, at most, one nucleic acid-less or one amino acid-less than the wild type full length sequence. Derivatives and analogs may be full length or other than full length, if said derivative or analog contains a modified nucleic acid or amino acid, as described infra. Derivatives or analogs of the chimeric peptides include, but are not limited to, molecules comprising regions that are substantially homologous in various embodiments, of at least 30%, 40%, 50%, 60%, 70%, 80%, 90% or preferably 95% amino acid identity when: (i) compared to an amino acid sequence of identical size; (ii) compared to an aligned sequence in that the alignment is done by a computer homology program known within the art (e.g., Wisconsin GCG software) or (iii) the encoding nucleic acid is capable of hybridizing to a sequence encoding the aforementioned peptides under stringent (preferred), moderately stringent, or non-stringent conditions. See, e.g., Ausubel, et al., *Current Protocols in Molecular Biology,* John Wiley and Sons, New York, N.Y., 1993.

Derivatives of the chimeric peptides may be produced by alteration of their sequences by substitutions, additions or deletions that result in functionally-equivalent molecules. Thus, the invention includes DNA sequences that encode substantially the same amino acid sequence. In another embodiment, one or more amino acid residues within the sequence of interest may be substituted by another amino acid of a similar polarity and net charge, thus resulting in a silent alteration. Substitutes for an amino acid within the sequence may be selected from other members of the class to which the amino acid belongs. For example, nonpolar (hydrophobic) amino acids include alanine, leucine, isoleucine, valine, proline, phenylalanine, tryptophan and methionine. Polar neutral amino acids include glycine, serine, threonine, cysteine, tyrosine, asparagine, and glutamine. Positively charged (basic) amino acids include arginine, lysine and histidine. Negatively charged (acidic) amino acids include aspartic acid and glutamic acid.

In particular embodiments, the chimeric peptides, and fragments, derivatives, homologs or analogs thereof, are related to animals (e.g., mouse, rat, pig, cow, dog, monkey, frog), or human opioids. Homologs (ie., nucleic acids encoding peptides derived from species other than human) or other related sequences (e.g., paralogs) can also be obtained by low, moderate or high stringency hybridization with all or a portion of the particular human sequence as a probe using methods well known in the art for nucleic acid hybridization and cloning. See, e.g., Ausubel et al., (eds.), 1993, *Current Protocols in Molecular Biology,* John Wiley and Sons, NY; and Kriegler, 1990, *Gene Transfer and Expression, A Laboratory Manual,* Stockton Press, NY.

In one embodiment, a nucleic acid sequence that is hybridizable to a nucleic acid sequence (or a complement of the foregoing) encoding the chimeric peptides, or a derivative of the same, under conditions of high stringency is provided: Step 1: Filters containing DNA are pretreated for 8 hours to overnight at 65° C. in buffer composed of 6×SSC, 50 mM Tris-HCl (pH 7.5), 1 mM EDTA, 0.02% PVP, 0.02% Ficoll, 0.02% BSA, and 500 µg/ml denatured salmon sperm DNA. Step 2: Filters are hybridized for 48 hours at 65° C. in the above prehybridization mixture to which is added 100 mg/ml denatured salmon sperm DNA and $5-20\times10^6$ cpm of $^{32}$P-labeled probe. Step 3: Filters are washed for 1 hour at 37° C. in a solution containing 2×SSC, 0.01% PVP, 0.01% Ficoll, and 0.01% BSA. This is followed by a wash in 0.1×SSC at 50° C. for 45 minutes. Step 4: Filters are autoradiographed. Other conditions of high stringency that may be used are well known in the art.

In a second embodiment, a nucleic acid sequence that is hybridizable to a nucleic acid sequence (or a complement thereof) encoding the chimeric peptides, or derivatives, under conditions of moderate stringency is provided: Step 1: Filters containing DNA are pretreated for 6 hours at 55° C. in a solution containing 6×SSC, 5×Denhardt's solution, 0.5% SDS and 100 mg/ml denatured salmon sperm DNA. Step 2: Filters are hybridized for 18–20 hours at 55° C. in the same solution with 5–20×106 cpm $^{32}$P-labeled probe added. Step 3: Filters are washed at 37° C. for 1 hour in a solution containing 2×SSC, 0.1% SDS, then washed twice for 30 minutes at 60° C. in a solution containing 1×SSC and 0.1% SDS. Step 4: Filters are blotted dry and exposed for autoradiography. Other conditions of moderate stringency that may be used are well-known in the art.

In a third embodiment, a nucleic acid that is hybridizable to a nucleic acid sequence disclosed in this invention or to a nucleic acid sequence encoding a the aforementioned peptides, or fragments, analogs or derivatives under conditions of low stringency: Step 1: Filters containing DNA are pretreated for 6 hours at 40° C. in a solution containing 35% formamide, 5×SSC, 50 mM Tris-HCl (pH 7.5), 5 mM EDTA, 0.1% PVP, 0.1% Ficoll, 1% BSA, and 500 µg/ml denatured salmon sperm DNA. Step 2: Filters are hybridized for 18–20 hours at 40° C. in the same solution with the addition of 0.02% PVP, 0.02% Ficoll, 0.2% BSA, 100 µg/ml salmon sperm DNA, 10% (wt/vol) dextran sulfate, and 5–20×106 cpm $^{32}$P-labeled probe. Step 3: Filters are washed for 1.5 hours at 55° C. in a solution containing 2×SSC, 25 mM Tris-HCl (pH 7.4), 5 mM EDTA, and 0.1% SDS. The wash solution is replaced with fresh solution and incubated an additional 1.5 hours at 60° C. Step 4: Filters are blotted dry and exposed for autoradiography. If necessary, filters are washed for a third time at 65–68° C. and re-exposed to film. Other conditions of low stringency that may be used are well known in the art (e.g., as employed for cross-species hybridizations). See also Shilo and Weinberg, *Proc Natl Acad Sci USA* 78: 6789–6792 (1981).

Design of Chimeric Peptides

Peptides with Affinity for the μ Receptor

The exogenous opioid peptide agonists for the μ receptor type include those listed in Table 1: α-endorphin, endomorphin-1, endomorphin-2, dermorphin, β-casomorphin (bovine or human), Morphiceptin, Leu-enkephalin, Met-enkephalin, DALDA, and PL107. Modifications of the peptides have resulted in very selective μ receptor ligands. These modifications can include amidation of the carboxyl terminus (—NH₂), the use of (D) amino acids in the peptide (e.g. DALDA), incorporation of small non-peptidyl moieties, as well as the modification of the amino acids themselves (e.g. alkylation or esterification of side chain R-groups). As in, for example, the compound DAMGO: Tyr-(D)Ala-Gly-Phe-NHCH₂CH₂OH.

TABLE 1

| SEQ ID NO: | μ receptor agonist | Sequence |
|---|---|---|
| 1 | α-endorphin | Tyr-Gly-Gly-Phe-Met-Thr-Ser-Glu-Ser-Gln-Thr-Pro-Leu-Val-Thr-NH₂ |
| 2 | endomorphin-1 | Tyr-Pro-Trp-Phe-NH₂ |
| 3 | endomorphin-2 | Tyr-Pro-Phe-Phe-NH₂ |
| 4 | dermorphin | Tyr-(D)Ala-Phe-Gly-Tyr-Pro-Ser-NH₂ |
| 5 | β-casomorphin (bovine) | Tyr-Pro-Phe-Pro-Gly-Pro-Ile |
| 6 | β-casomorphin (human) | Tyr-Pro-Phe-Val-Glu-Pro-Ile |
| 7 | Morphiceptin | Tyr-Pro-Phe-Pro-NH₂ |
| 8 | Leu-enkephalin | Tyr-Gly-Gly-Phe-Leu |
| 9 | Met-enkephalin | Tyr-Gly-Gly-Phe-Met |
| 10 | DALDA | Tyr-(D)Arg-Phe-Lys-NH₂ |
| 11 | PL017 | Tyr-Pro-(N-Me)Phe-(D)Pro-NH₂ |

Peptides with Affinity for the δ Receptor

Other suitable opioid peptide moieties include the δ receptor agonists listed in Table 2. Those with highest receptor selectivity generally are enkephalin-derived peptides. For example, DADLE has a three to ten fold higher selectivity for the δ receptor than the μ receptor. Modifications of the parent enkephalin sequence results in two groups of peptide analogs. The first group is a series of linear analogs, for example, DSLET. The second group, all rigid cyclic analogs, includes DPDPE (where Pen is penicillamine, or 3-mercapto-(D)Valine). In binding assays, these analogs show an 100-fold affinity for the δ receptor over the μ-receptor and a 1000-fold increase over the κ-receptor. Additional pseudopeptide analogs, either linear or cyclic, also display high selectivity to the δ receptor, for example Tyr-Tic-Phe-Phe, where Tic is L-1,2,3,4-tetrahydroisoquinoline-3-carboxylic acid. Schiller, et al., *J. Med. Chem.* 36: 3182–3187 (1993).

TABLE 2

| SEQ ID NO: | δreceptor agonists | Sequence |
|---|---|---|
| 12 | DADLE | Tyr-(D)Ala-Gly-Phe-(D)Leu |
| 13 | DSLET | Tyr-(D)Ser-Gly-Phe-Leu-Thr |
| 14 | DPDPE | Tyr-(D)Pen-Gly-Phe-(D)Pen (cyclic) |

TABLE 2-continued

| SEQ ID NO: | δreceptor agonists | Sequence |
|---|---|---|
| 15 | deltorphin I | Tyr-(D)Ala-Phe-Asp-Val-Val-Gly-NH₂ |
| 16 | deltorphin II | Tyr-(D)Ala-Phe-Glu-Val-Val-Gly-NH₂ |
| 17 | dermenkephalin | Tyr-(D)Met-Phe-His-Leu-Met-Asp-NH₂ |

Peptides with Affinity for the κ Receptor

Opioid moieties also include Dynorphin ("DYN") related peptides, which are endogenous peptide agonists for the κ receptor. Some representative peptides are shown in Table 3. The propeptide, pro-dynorphin, is processed into peptides of different lengths and with different receptor selectivities. Several of these peptides, including Dynorphin A, DYN(1-8), and DYN(1-13) are found in the CNS of vertebrates in physiologically significant concentrations. Several dynorphin analogs have been generated by substitution of D-amino acids at position 8 (Ile) or 10 (Pro). Additionally cyclic dynorphin analogs with high κ receptor selectivity have been generated: e.g., Tyr-Gly-Gly-Phe-Leu-Arg-Arg-Cys-Arg-Pro-Lys-Leu-Cys-NH₂ (SEQ ID NO: 44), where the two Cysteines are engaged in a disulfide bond, to create a six amino acid ring.

TABLE 3

| SEQ ID NO: | κ receptor agonists | Sequence |
|---|---|---|
| 18 | Dynorphin A | Tyr-Gly-Gly-Phe-Leu-Arg-Arg-Ile-Arg-Pro-Lys-Leu-Lys-Trp-Asp-Asn-Gln |
| 19 | DYN (1-8) | Tyr-Gly-Gly-Phe-Leu-Arg-Arg-Ile |
| 20 | DYN (1-13) | Tyr-Gly-Gly-Phe-Leu-Arg-Arg-Ile-Arg-Pro-Lys-Leu-Lys |

Peptides with Affinity for NK₁ Receptor: Substance P Peptides

The SP moiety of the chimeric peptide is designed to bind to the NK₁ receptor. SP is an 11 acid peptide, which has a number of different natural and synthetic analogs. A representative group is shown in Table 4, below. A number of SP amino-terminal fragments and modified peptides have a high degree of specificity for the NK₁ receptor relative to NK₂ and NK₃ receptors. This specificity can be increased by esterification of the carboxy terminal amide. Other modifications include the generation of cyclic molecules (e.g. via Cys-Cys disulfide bridges), the incorporation of non-peptidyl moieties (e.g. spirolactones as discussed by Ward in *J. Med. Chem.* 33: 1848–1851 (1990)). Additionally, SP and SP analogs can be made more stable by using D-amino acids. A representative listing of SP and its related family of compounds is provided in Table 4 below.

TABLE 4

| SEQ ID NO: | Compound | Sequence |
|---|---|---|
| 21 | SP | Arg-Pro-Lys-Pro-Gln-Gln-Phe-Phe-Gly-Leu-Met-NH₂ |
| 22 | SP-Glycine | Arg-Pro-Lys-Pro-Gln-Gln-Phe-Phe-Gly-Leu-Met-Gly-NH₂ |
| 23 | SP-Glycine-Lysine | Arg-Pro-Lys-Pro-Gln-Gln-Phe-Phe-Gly-Leu-Met-Gly-Lys-NH₂ |
| 24 | SP-Glycine-Lysine-Arginine | Arg-Pro-Lys-Pro-Gln-Gln-Phe-Phe-Gly-Leu-Met-Gly-Lys-Arg-NH₂ |

TABLE 4-continued

| SEQ ID NO: | Compound | Sequence |
|---|---|---|
| 25 | SP-Glycine Methyl Ester | Arg-Pro-Lys-Pro-Gln-Gln-Phe-Phe-Gly-Leu-Met-Gly-O$^{me}$ |
| 26 | SP-Glycine-Lycine-Methyl Ester | Arg-Pro-Lys-Pro-Gln-Gln-Phe-Phe-Gly-Leu-Met-Gly-Lys-O$^{me}$ |
| 27 | SP-Glycine-Lysine-Arginine Methyl Ester | Arg-Pro-Lys-Pro-Gln-Gln-Phe-Phe-Gly-Leu-Met-Gly-Lys-Arg-O$^{me}$ |
| 28 | SP-Glycine-Elthyl Ester | Arg-Pro-Lys-Pro-Gln-Gln-Phe-Phe-Gly-Leu-Met-Gly-O$^{eth}$ |
| 29 | SP-Glycine-Lysine Ethyl Ester | Arg-Pro-Lys-Pro-Gln-Gln-Phe-Phe-Gly-Leu-Met-Gly-Lys-O$^{eth}$ |
| 30 | SP-Glycine-Lysine-Arginine Ethyl Ester | Arg-Pro-Lys-Pro-Gln-Gln-Phe-Phe-Gly-Leu-Met-Gly-Lys-Arg-O$^{eth}$ |
| 31 | SP/1-4# | Arg-Pro-Lys-Pro-NH$_2$ |
| 32 | SP/1-7# | Arg-Pro-Lys-Pro-Gln-Gln-Phe-NH$_2$ |
| 33 | SP/1-9# | Arg-Pro-Lys-Pro-Gln-Gln-Phe-Phe-Gly-NH$_2$ |
| 34 | [D-Pro2, D-Phe7, D-Trp9]-SP | Arg-(D)Pro-Lys-Pro-Gln-Gln-(D)Phe-Phe(D)Trp-Leu-Met-NH$_2$ |
| 35 | [D-Pro2, D-Phe7, D-Trp9]-SP-(Glycine) | Arg-(D)Pro-Lys-Pro-Gln-Gln-(D)Phe-Phe-(D)Trp-Leu-Met-Gly-NH$_2$ |
| 36 | [D-Pro2, D-Trp7, D-Trp9]-SP | Arg-(D)Pro-Lys-Pro-Gln-Gln-(D)Trp-Phe-(D)Trp-Leu-Met-NH$_2$ |
| 37 | [D-Pro2, D-Trp7, D-Trp9]-SP-Glycine | Arg-(D)Pro-Lys-Pro-Gln-Gln-(D)Trp-Phe-(D)Trp-Leu-Met-Gly-NH$_2$ |
| 38 | [Cys3, Cys6, Tyr8, Pro10]-SP | Arg-Pro-Cys-Pro-Gln-Cys-Phe-Tyr-Gly-Pro-Met-NH$_2$ |
| 39 | [Glu 6]-SP/6-11 | Glu-Phe-Phe-Gly-Leu-Met-NH$_2$ |
| 40 | Septide | Glu-Phe-Phe-Pro-Leu-Met-NH$_2$ |
| 41 | Sanktide | HOOC—CH$_2$—CH$_2$—CO-Asp-Phe-(N-Me)Phe-Gly-Leu-Met-NH$_2$ |

Figure 2:
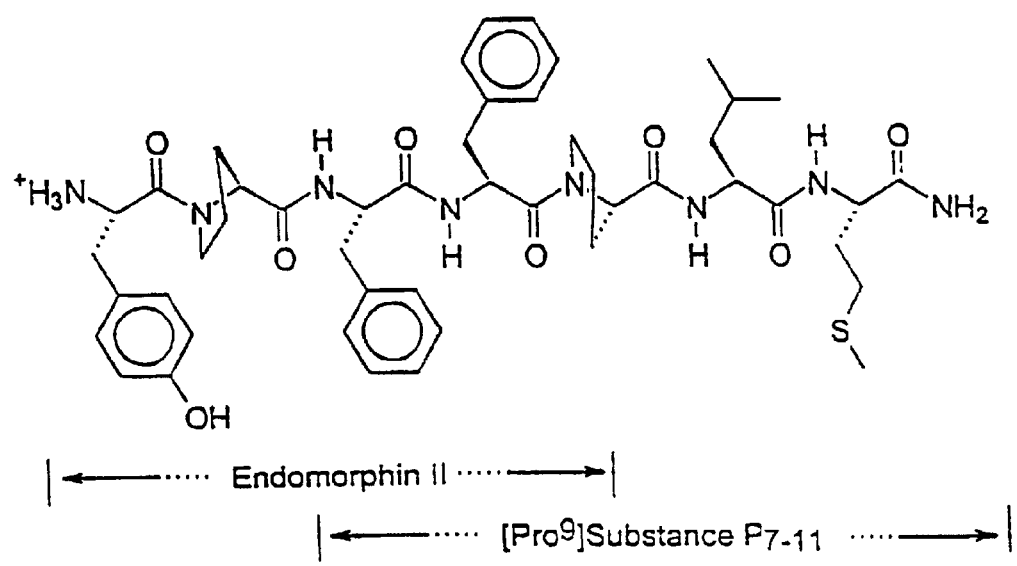
FIG. 2 is a schematic representation of the chimeric peptide ESP6.

If the target of the chimeric peptide is the μ receptor, the opioid agonist moiety is chosen from those shown to be selective for that receptor, e.g. those in Table 1. If the opioid target receptor is the δ receptor, the opioid agonist moiety is selected from the group consisting of DADLE, DSLET, DPDPE, deltorphin I, deltorphin II and dermenkephalin. If the target opioid receptor of the chimeric peptide is the κ-receptor, the opioid agonist moiety is selected from the group consisting of the dynorphin peptides. The chimeric peptide may be synthesized to have a plurality of opioid moieties. These opioid moieties may be directed to any combination of the opioid receptors or may be directed to the same receptor type. Furthermore, a chimera may be synthesized to contain a plurality of SP moieties per each opioid moiety. In one embodiment, the novel chimeric peptide is ESP7, SEQ ID NO:42 (FIG. 1). Because it includes endomorphin-2 at the N-terminus and SP (7-11) at the C-terminus, ESP7 is designed to bind to the μ receptor and the NK$_1$ receptor. One ESP7 derivative is ESP6, or Pro 5 ESP7: Tyr-Pro-Phe-Phe-Pro-Leu-Met-NH$_2$ (FIG. 2, SEQ ID NO:43).

Pharmaceutical Compositions

The chimeric peptides of the invention, and derivatives can be incorporated into pharmaceutical compositions suitable for administration. Such compositions typically comprise the peptide and a pharmaceutically acceptable carrier. As used herein, "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions. Modifications can be made to the peptide of the present invention to affect solubility or clearance of the peptide. These molecules may also be synthesized with D-amino acids to increase resistance to enzymatic degradation. If necessary, the chimeric peptides can be co-administered with a solubilizing agent, such as cyclodextran.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., chimeric peptide) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Nucleic acid molecules encoding the chimeric peptides of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *PNAS* 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells that produce the gene delivery system.

The pharmaceutical compositions can be included in a container, pack, or dispenser together with instructions for administration.

Treatment of Pain

The invention further provides methods of treating a mammal for pain by administering a pharmaceutical composition (as described above) in order to produce analgesia in the patient. One method to assess the analgesic properties of the chimeric peptides is the tail flick test, which is administered to rats following intrathecal, intracerebroventricular, and intraperitoneal administration. The effects of opioid antagontsts (e.g., naltrexone) and $NK_1$ antagonists (e.g., RP67580) on the activity of the peptides can be assessed according to methods common in the art.

In order that this invention may be better understood, the following examples are set forth. These examples are for the purposes of illustration only and are not to be construed as limiting the scope of this invention in any manner.

EXAMPLE 1

In vitro Binding of ESP7 to Opioid and SP Receptors in Rat Brain Preparations

In order to assess the binding affinity of ESP7 to opioid and SP receptor, binding assays to opioid and SP receptors were performed with crude rat brain plasma membranes prepared using a modified procedure of Zadina. Zadina et al., *Life Sci*, 55: 461–466 (1994). These assays showed that ESP7 has a strong affinity for both the $\mu$ receptor and the $NK_1$ receptor in rat brain.

For binding assays to opioid receptors, frozen rat brains (−80° C.) were homogenized in 40 volumes of standard Tris buffer (50 mM Tris HCl (pH 7.4), 0.2 mg/ml BSA, 2.5 mM EDTA, 40 $\mu$g/ml bacitracin, 30 $\mu$g/ml bestatin and 5 mM $MgCl_2$) and centrifuged at 15,000×g for 20 minutes. 100 mM NaCl was added to the buffer, in order to remove endogenous ligands, and the centrifugation was repeated. After a wash with standard buffer, the membrane preparation was finally resuspended in 10 volumes of incubation buffer (standard buffer with 4 $\mu$g/ml leupeptin and 2 $\mu$g/ml chymostatin). The same procedure was followed for the SP receptor except the wash with NaCl was eliminated and 5 mM $MgCl_2$ was replaced with 3 mM $MnCl_2$. The brain homogenates were used on the day of preparation.

Binding assays for the $\mu$ receptor were performed at 4° C. for 90 minutes, as described in Zadina et al., *Life Sci*, 55: 461–466 (1994). A final volume of 0.35 mL was used which contained incubation buffer (described above), brain homogenate, and 1.85 nM [$^3$H]DAMGO with or without competing peptide (DAMGO or ESP7). Nonspecific binding was determined with 10 μM DAMGO. After incubation the samples were filtered on a Brandell-Harvester using an appropriate GF/B filter soaked in 50 mM Tris HCl (pH 7.4) and 0.5% PEI. Scintillation fluid was added to the filters in order to solubilize the membranes, and a beta-counter was used to quantify radioactivity.

A procedure similar to the opioid binding assay was followed for the SP receptor except the SP assays were performed at room temperature for 75 minutes using 23 fmol of [$^{125}$I]BH-SP. 10 μM SP defined the non-specific binding. After filtration, the radioactivity was determined on a gamma-counter.

Figure 3:
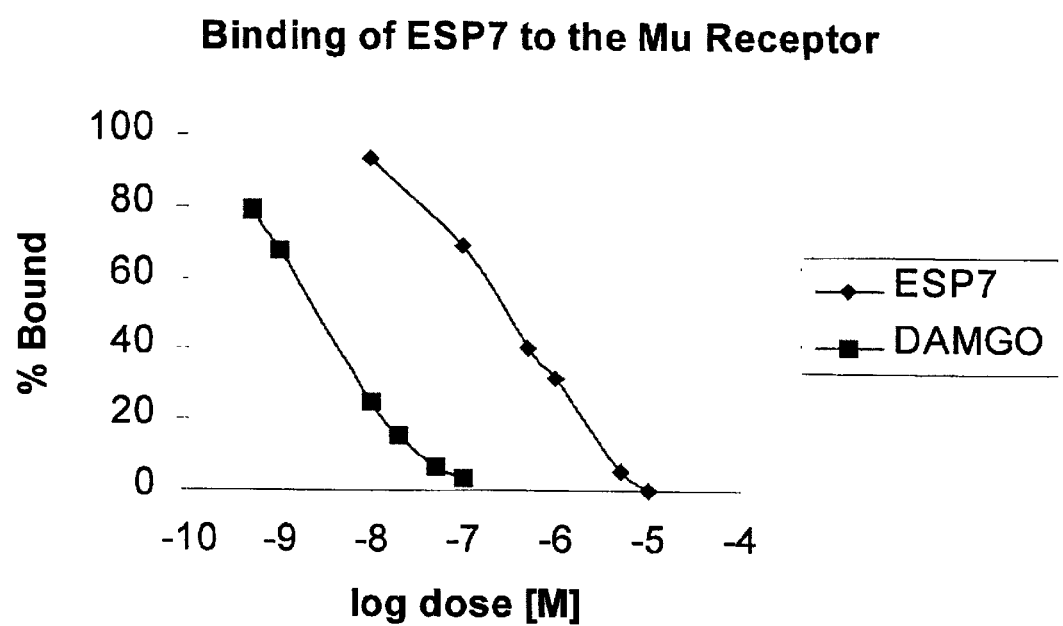
FIG. 3 is a graph illustrating the binding affinity of ESP7 to the μ receptor.
Figure 4:
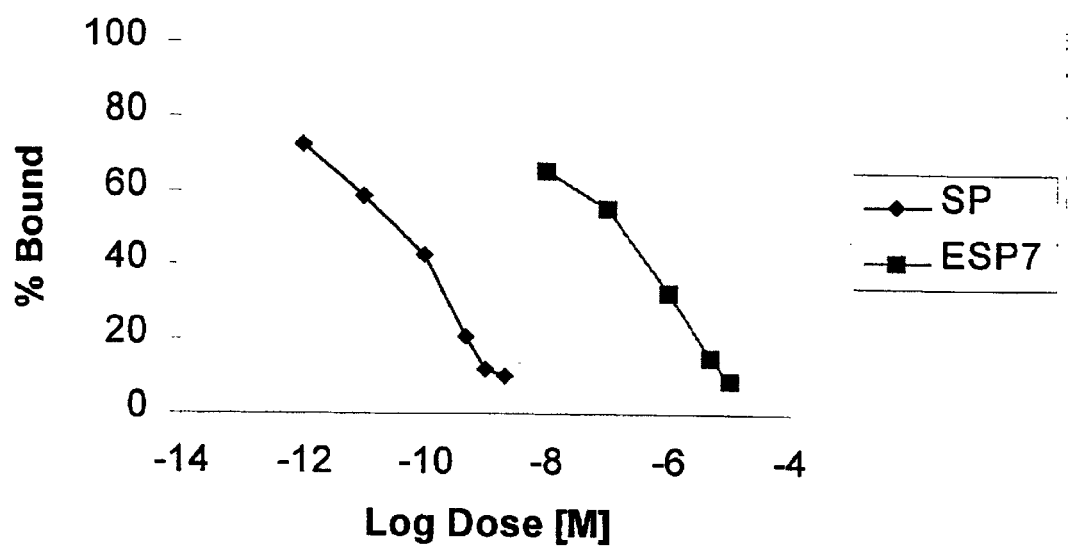
FIG. 4 is a graph illustrating the binding affinity of ESP7 to the $NK_1$ receptor.
Figure 8:
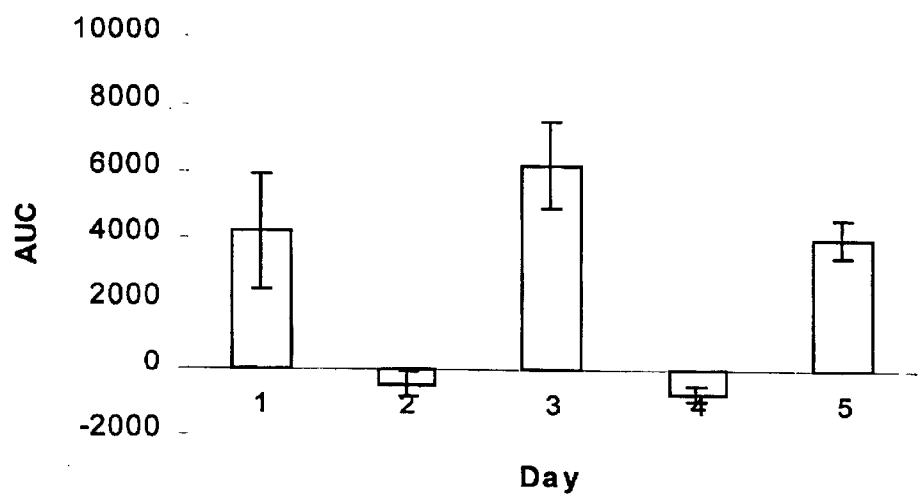
FIG. 8 is a graph illustrating the analgesic effect in rats over time of 0.2 μg of ESP7 antagonized with on days 2 and 4 with 0.2 μg of naltrexone.

As seen in the FIG. 3, DAMGO had a $K_d$ of approximately 3 nM (FIG. 8). ESP7 had a $K_d$ of approximately 300 nM, illustrating that ESP7 possesses significant affinity for the μ receptor. As seen in FIG. 4, SP had a $K_d$ of approximately 0.03 nM, while ESP7 had a $K_d$ of approximately 200 nM. Thus, ESP7 has significant affinity for the $NK_1$ receptor, and, as expected, ESP7 bound specifically to and had significant binding affinity for both the μ receptor and the $NK_1$ receptor.

EXAMPLE 2

Characterization of the Analgesic Properties of ESP7

ESP7 was tested clinically in rats to determine analgesic effect and tolerance. The classical tail flick test was used to measure pain response and thermal pain was mimicked using a heat source. This system was controlled using standard opioids. The drug was administered with cyclodextran to increase solubility of the peptide in an aqueous solution.

2.1 Intrathecal Administration of ESP7 in Rats and the Effects of Naltrexone and RP67580 Blockades Intrathecal administration of ESP7 produced long-lasting analgesia without any significant development of tolerance. The opioid antagonist naltrexone blocked this analgesia, indicating that the analgesia was opioid in nature. Additionally, when the SP portion was antagonized with RP67580, an $NK_1$ antagonist, tolerance to the drug developed within three days. These results indicate that the SP moiety of ESP7 does not contribute to the analgesia, but rather plays an integral role in preventing the development of tolerance.

Adult male Sprague Dawley rats (200–250 g) were implanted with chronic indwelling intrathecal catheters using a modified protocol of Yaksh and Rudy, *Physiol. Behav.,* 17: 1031–1036 (1976). Catheters were made of silastic tubing, had an inside diameter of 0.012" and an outside diameter of 0.025", and measured a total of 11.5 cm with 7.5 cm inserted into the intrathecal space to level T13-L1. The rats were anesthetized throughout the surgery with 5.0% isoflurane. The catheter was inserted through the alanto-occipital membrane and into the intrathecal space using a guide wire. Sutures were used to secure the placement of the catheter. The rats were allowed to recover from surgery for 3–4 days and any rats with neurological impairment were not used for analgesic measurements. Rats were housed separately in a 12 hr light-dark cycle with free access to food and water. During their recovery from surgery, rats were habituated to the laboratory environment and analgesic testing apparatus.

For measurement of the thermal anti-nociceptive properties of the peptides of interest, the tail flick test was employed. Rats were first habituated to the tail flick chamber. During testing, the rats were placed in the chamber and a light source, which generated heat, was directed at their tail. The latency to remove the tail was recorded. The baseline latency was approximately 3.5 sec and the cutoff latency was 10 sec to avoid tissue damage. Three measurements were made at each pre- and post-treatment time point and the results were averaged. Responses were expressed as % maximum possible effect:

$$\% \, MPE = \frac{\text{post} - \text{treatment latency} - \text{baseline latency}}{\text{cutoff time} - \text{baseline}} \times 100$$

After testing, the rats were sacrificed and the correct placement of the catheter was verified by dissection of the spinal cord.

Rats were given doses of 1.0 μg (FIG. 5), 0.2 μg (FIG. 6), and 0.05 μg (FIG. 7) of ESP7. The desired concentration of the compound (in 10 μl) was injected into the catheter followed by 10 μl saline flush to fill the dead volume. ESP7 was combined with two molecules of cyclodextrin (ESP7+ 2CD) to increase solubility. Ultimately, cyclodextrin can form reversible complexes with lipophilic compounds such as ESP7 to increase their solubility, decrease their clearance from the spinal cord and enhance their duration of action.

Figure 5:
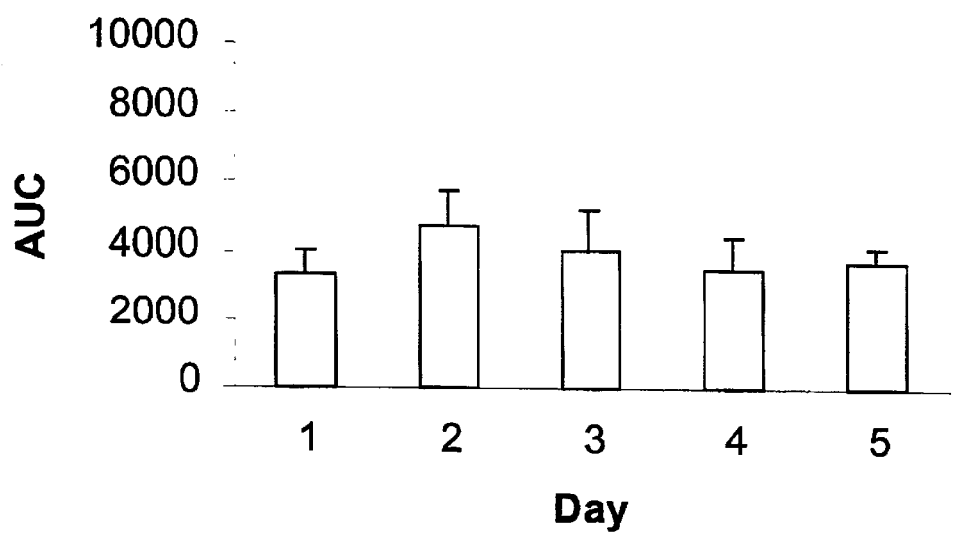
FIG. 5 is a graph illustrating the analgesic effect in rats over time of 1.0 μg of ESP7 administered intrathecally.
Figure 6:
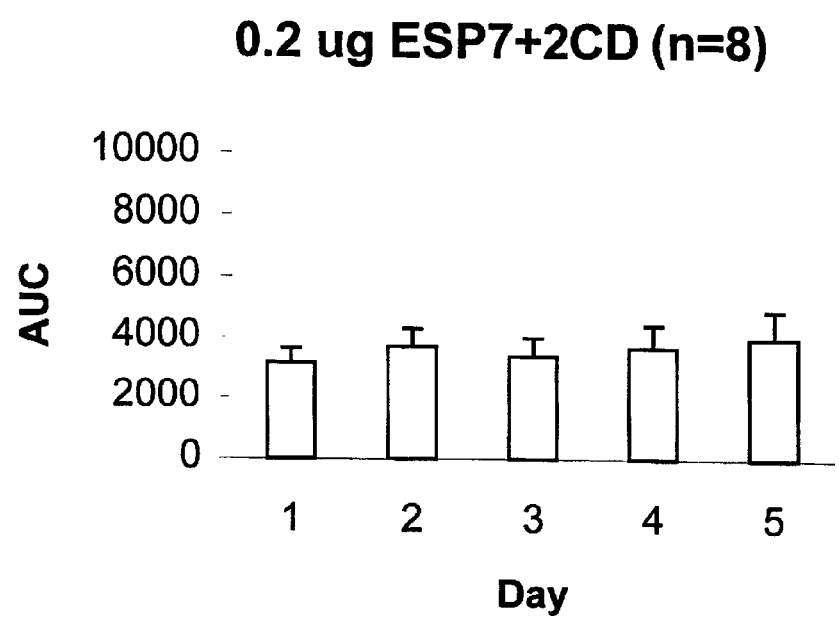
FIG. 6 is a graph illustrating the analgesic effect in rats over time of 0.2 μg of ESP7 administered intrathecally.
Figure 7:
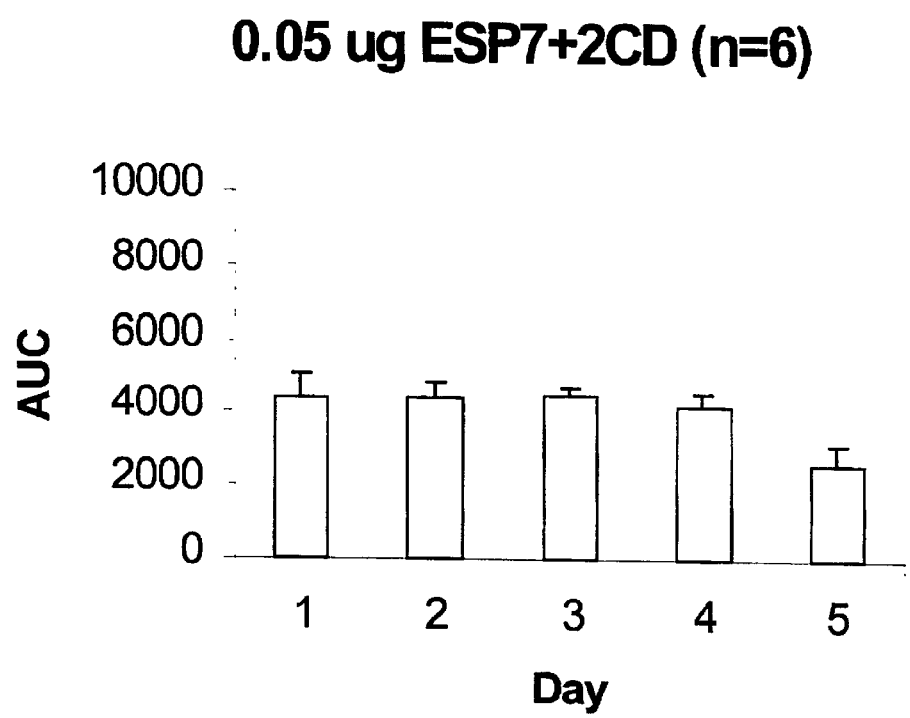
FIG. 7 is a graph illustrating the analgesic effect in rats of 0.05 μg of ESP7 administered intrathecally.

As shown in FIG. 5, the 1.0 μg dose produced a low level of prolonged analgesia for five days. More interestingly, no tolerance developed to the effects of ESP7+2CD (p>0.05). As shown in FIG. 6, the analgesia produced by 0.2 μg remained at the same level for five days (p>0.05). As shown in FIG. 7, however, some tolerance did appear to develop at the 0.05 μg dose on day 5 (p=0.014). As a control, 1.0 μg of 2-cyclodextrin was administered intrathecally with no significant effect (p>0.05) (data not shown).

To examine whether the analgesia produced was opioid in nature, the opioid receptor was antagonized with naltrexone. On the days indicated below, naltrexone, was administered 10 min prior to ESP7+2CD. As shown in FIG. 8, 0.2 μg ESP7+2CD produced analgesia on Days 1, 3, and 5, but not on Days 2 and 4 when naltrexone was administered (p=0.0042). Similar results were seen with the 1.0 μg of ESP7+2CD, where naltrexone again significantly blocked the analgesia (p=0.0009) (data not shown). Naltrexone actually produced some hyperalgesia when given with both doses of ESP7+2CD, unmasking the nociceptive activity of SP. In addition, the naltrexone blockade was reversible once the drug had been removed. A control experiment illustrated that naltrexone alone produced no change in analgesia (p>0.05)(data not shown).

Figure 9:
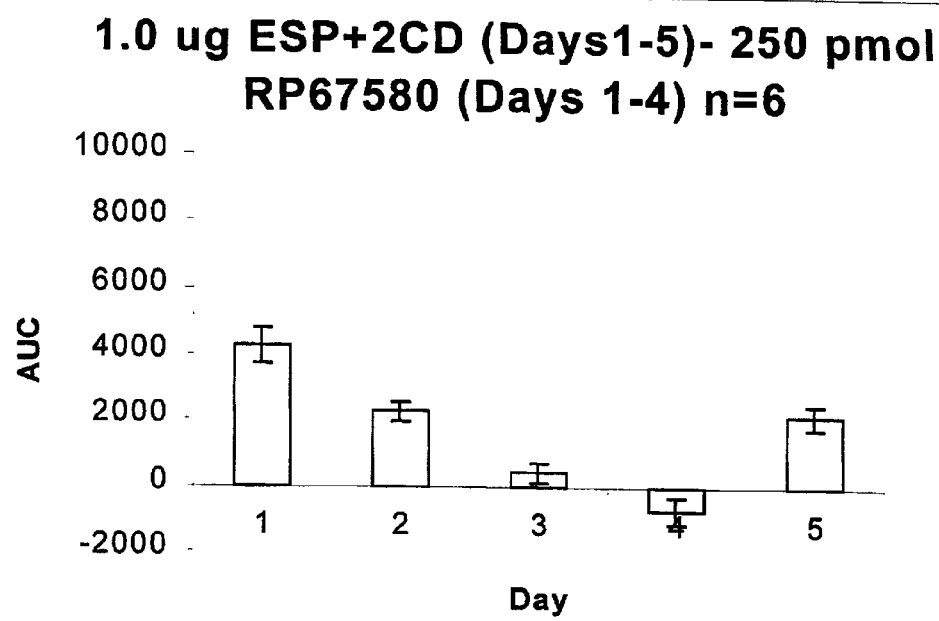
FIG. 9 is a graph illustrating the analgesic effect in rats over time of 1.0 µg of ESP7 antagonized with RP67580 on days 1–4.

To examine whether the reduced tolerance exhibited in rats treated with ESP7 was SP mediated, the $NK_1$ receptor was antagonized with RP67580, a specific $NK_1$ antagonist with high affinity for the rat $NK_1$ receptor. RP67580 (250 pmol) was administered IT prior to 1.0 μg ESP7+2CD. As seen in FIG. 9, ESP7+2CD produced significant analgesia on Day 1, but tolerance developed to this analgesia within three days (p<0.0001). Slight hyperalgesia was present on Day 4. On Day 5, the $NK_1$ antagonist was removed and a partial rescue of the analgesia occurred. The level of analgesia on Day 5 reached a level similar to Day 2 (p>0.05). RP67580 alone had no effect on the level of analgesia (p>0.05). Therefore, ESP7 administered intrathecally was able to induce analgesia while minimizing the development of tolerance.

2.2 Intracerebroventricular Administration of ESP7 in Rats

Adult male Sprague Dawley rats weighing 200–250 g were used. Before surgery, the rats were anesthetized with 0.2–0.3 mL of xylazine (10%) and ketamine (90%). Rats were positioned in a stereotaxic apparatus and the bregma was located. To reach the lateral ventricle, a hole was drilled 0.8 mm caudal and 1.4–1.5 mm left or right of the bregma. The catheter was inserted 4.5 mm deep into the brain and 4.0 cm of polyethylene tubing was connected to the end to the catheter. Screws and dental cement were used to secure the catheter in place. After suturing the skin, the rats were allowed to recover from surgery for 4–5 days. Each rat was housed separately in a 12 hr light-dark cycle with free access to food and water. Rats with any neurological problems were not used in the analgesic testing.

The tail flick assay was used to measure analgesia as described above in Example 2.1. Briefly, the rats were first habituated to the tail flick chamber. During testing, the rats were placed in the chamber and a light source, which generated heat, was directed at their tail. The latency to remove the tail was recorded. The baseline latency was approximately 3.5 sec and the cutoff latency was 10 sec to avoid tissue damage. Three measurements were made at each pre- and post-treatment time point and the results were averaged. Responses were expressed as % maximum possible effect (MPE):

$$\% \ MPE = \frac{\text{post}-\text{treatment latency}-\text{baseline latency}}{\text{cutoff time}-\text{baseline}} \times 100$$

After resting the rats were sacrificed and the correct placement of the catheter was verified.

Figure 10:
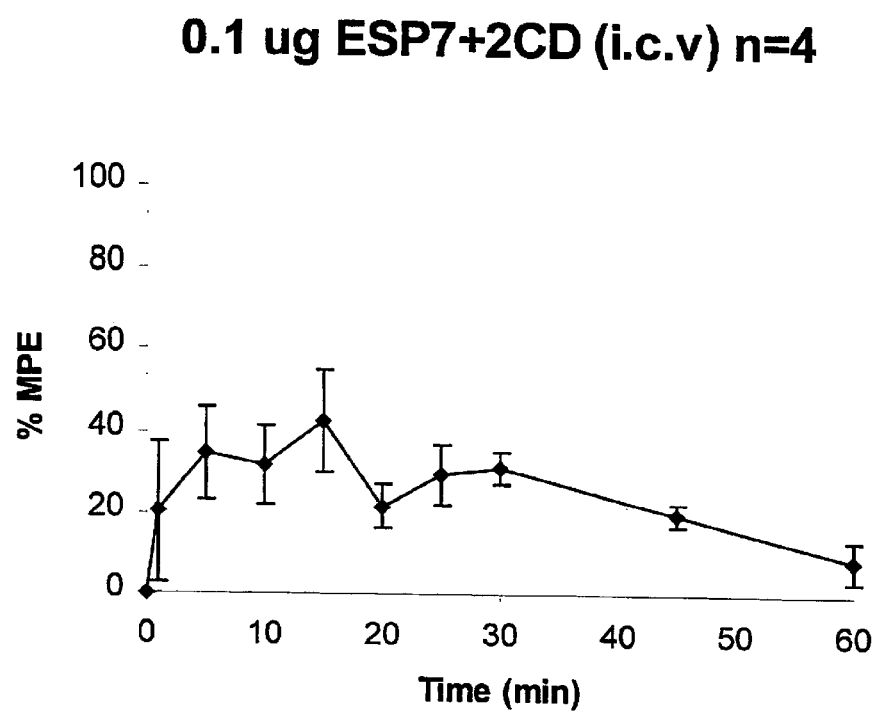
FIG. 10 is a graph illustrating the analgesic effect in rats over time of 0.1 µg of ESP7 administered intracerebroventricularly.

As shown in FIG. 10, 0.1 µg ESP7+2CD produced a low level of analgesia that dissipated after one hour. ESP7 (1.0 µg) also produced analgesia (data not shown).

2.3 Intraperitoneal Administration of ESP7 in Rats

ESP7 was administered intraperitoneally in order to assess the effectiveness of ESP7 systemically. The tail flick assay was used to measure analgesia as described above in Example 2.1. Briefly, the rats were first habituated to the tail flick chamber. During testing, the rats were placed in the chamber and a light source, which generated heat, was directed at their tail. The latency to remove the tail was recorded. The baseline latency was approximately 3.5 sec and the cutoff latency was 10 sec to avoid tissue damage. Three measurements were made at each pre- and post-treatment time point and the results were averaged. Responses were expressed as % maximum possible effect (MPE):

$$\% \ MPE = \frac{\text{post}-\text{treatment latency}-\text{baseline latency}}{\text{cutoff time}-\text{baseline}} \times 100$$

Figure 11:
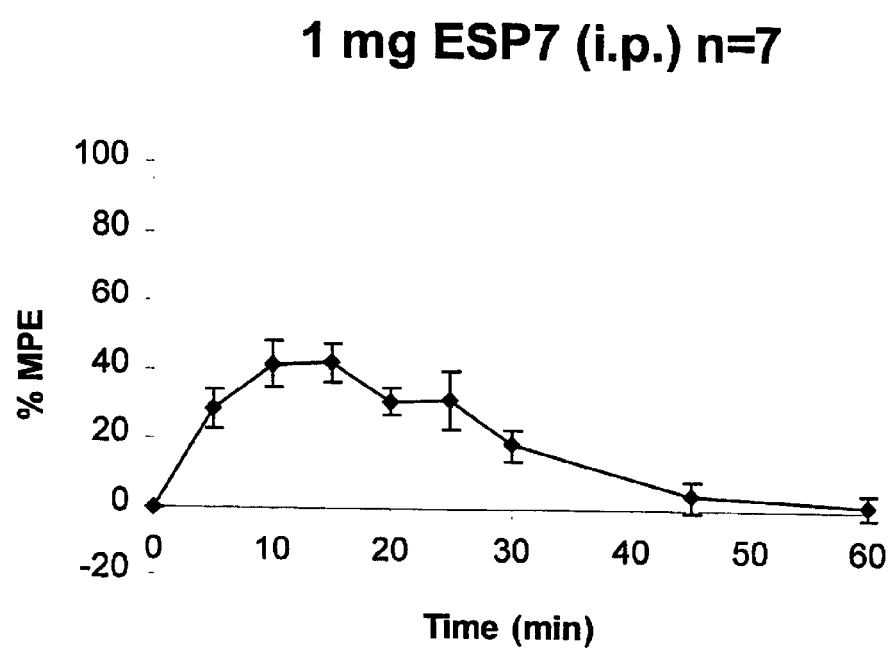
FIG. 11 is a graph illustrating the analgesic effect in rats over time of 1 mg of ESP7 administered intraperitoneally.

As seen in FIG. 11, 1 mg of ESP7 produced analgesia as seen with intrathecal administration. In addition, 3 mg of ESP7+2CD also produced analgesia similar to that seen with intrathecal administration (data not shown). A dose of 1 mg of ESP7+2CD was ineffective, thus a dose of 3 mg was chosen to account for the presence of two molecules of cyclodextrin (data not shown).

EQUIVALENTS

From the foregoing detailed description of the specific embodiments of the invention, it should be apparent that unique chimeric analgesic peptides have been described. Although particular embodiments have been disclosed herein in detail, this has been done by way of example for purposes of illustration only, and is not intended to be limiting with respect to the scope of the appended claims which follow. In particular, it is contemplated by the inventor that various substitutions, alterations, and modifications may be made to the invention without departing from the spirit and scope of the invention as defined by the claims. For instance, the choice of the particular opioid moiety, or the particular SP moiety is believed to be a matter of routine for a person of ordinary skill in the art with knowledge of the embodiments described herein.

What is claimed is:

1. A chimeric peptide comprising an agonist μ opioid receptor binding moiety at its N-terminus and an agonist Substance P receptor binding moiety at its C-terminus, wherein said peptide induces analgesia.

2. The peptide of claim 1 wherein the N-terminal amino acid residue of said opioid receptor binding moiety is a free amine.

3. The peptide of claim 2 wherein the N-terminal amino acid residue of said opioid receptor binding moiety is Tyr.

4. The peptide of claim 3 wherein said opioid receptor binding moiety is a peptide having any one of SEQ ID Nos: 1–11, or N-terminal fragment.

5. The peptide of claim 3 wherein said opioid receptor binding moiety is endomorphin 1, endomorphin 2, or N-terminal fragment.

6. The peptide of claim 5 wherein said opioid receptor binding moiety is a peptide having SEQ ID No: 2 or 3, or N-terminal fragment.

7. The peptide of claim 1, wherein said agonist Substance P receptor binding moiety comprises Substance P, or C-terminal Substance P fragment.

8. The peptide of claim 1, wherein the —COOH moiety of the C-terminal amino acid residue of said Substance P receptor binding moiety is protected.

9. The peptide of claim 8 wherein the —COOH moiety of the C-terminal amino acid residue of said Substance P receptor binding moiety is amidated.

10. The peptide of claim 9 wherein the C-terminal amino acid residue of said Substance P receptor binding moiety is Met-NH$_2$.

11. The peptide of claim 10 wherein said Substance P receptor binding moiety is a peptide having any one of SEQ ID Nos: 21, 36 and 38–41, or C-terminal fragment.

12. The peptide of claim 1 wherein the opioid receptor binding moiety is endomorphin 1, endomorphin 2, or N-terminal fragment thereof; and the Substance P receptor binding moiety is Substance P, or C-terminal fragment thereof.

13. The chimeric peptide of claim 1 wherein the peptide has SEQ ID No: 42.

14. The chimeric peptide of claim 1 wherein the peptide has SEQ ID No: 43.

15. A pharmaceutical composition comprising the peptide of claim 1 and a pharmaceutically acceptable diluent.

16. The pharmaceutical composition of claim 15, further comprising an adjuvant.

17. The pharmaceutical composition of claim 15 wherein the N-terminal amino acid residue of said opioid receptor binding moiety is a free amine.

18. The pharmaceutical composition of claim 17 wherein the N-terminal amino acid residue of said opioid receptor binding moiety is Tyr.

19. The pharmaceutical composition of claim 18 wherein said opioid receptor binding moiety is a peptide having any one of SEQ ID Nos: 1–11, or N-terminal fragment.

20. The pharmaceutical composition of claim 18 wherein said opioid receptor binding moiety is endomorphin 1, endomorphin 2, or N-terminal fragment.

21. The pharmaceutical composition of claim 20 wherein said opioid receptor binding moiety is a peptide having SEQ ID No: 2 or 3, or N-terminal fragment.

22. The pharmaceutical composition of claim 15, wherein said agonist Substance P receptor binding moiety comprises Substance P, or C-terminal Substance P fragment.

23. The pharmaceutical composition of claim 15, wherein the —COOH moiety of the C-terminal amino acid residue of said Substance P receptor binding moiety is protected.

24. The pharmaceutical composition of claim 23 wherein the —COOH moiety of the C-terminal amino acid residue of said Substance P receptor binding moiety is amidated.

25. The pharmaceutical composition of claim 24 wherein the C-terminal amino acid residue of said Substance P receptor binding moiety is Met-NH$_2$.

26. The pharmaceutical composition of claim 25 wherein said Substance P receptor binding moiety is a peptide having any one of SEQ ID Nos: 21, 36 and 38–41, or a C-terminal fragment.

27. The pharmaceutical composition of claim 15 wherein the opioid receptor binding moiety is endomorphin 1, endomorphin 2, or N-terminal fragment thereof; and the Substance P receptor binding moiety is Substance P, or C-terminal fragment thereof.

28. The pharmaceutical composition of claim 15 wherein the peptide has SEQ ID No: 42.

29. The pharmaceutical composition of claim 15 wherein the peptide has SEQ ID No: 43.

* * * * *

SEQUENCE LISTING

<160> NUMBER OF SEQ ID NOS: 43

<210> SEQ ID NO 1
<211> LENGTH: 15
<212> TYPE: PRT
<213> ORGANISM: Artificial Sequence
<220> FEATURE:
<223> OTHER INFORMATION: Description of Artificial Sequence: recombinant

<400> SEQUENCE: 1

Tyr Gly Gly Phe Met Thr Ser Glu Ser Gln Thr Pro Leu Val Thr
 1               5                  10                  15

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: recombinant

<400> SEQUENCE: 2

Tyr Pro Trp Phe
 1

```
<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence: recombinant

<400> SEQUENCE: 3

Tyr Pro Phe Phe
  1

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: recombinant

<400> SEQUENCE: 4

Tyr Ala Phe Gly Tyr Pro Ser
  1               5

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: recombinant

<400> SEQUENCE: 5

Tyr Pro Phe Pro Gly Pro Ile
  1               5

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: recombinant

<400> SEQUENCE: 6

Tyr Pro Phe Val Glu Pro Ile
  1               5

<210> SEQ ID NO 7
<211> LENGTH: 4
<212> TYPE: PRT
<213> ORGANISM: Artificial Sequence
<220> FEATURE:
<223> OTHER INFORMATION: Description of Artificial Sequence: recombinant

<400> SEQUENCE: 7

Tyr Pro Phe Pro
  1

<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence: recombinant

<400> SEQUENCE: 8

Tyr Gly Gly Phe Leu
  1               5
```

```
<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence: recombinant

<400> SEQUENCE: 9

Tyr Gly Gly Phe Met
 1               5

<210> SEQ ID NO 10
<211> LENGTH: 4
<212> TYPE: PRT
<213> ORGANISM: Artificial Sequence
<220> FEATURE:
<223> OTHER INFORMATION: Description of Artificial Sequence: recombinant

<400> SEQUENCE: 10

Tyr Pro Phe Pro
 1

<210> SEQ ID NO 11
<211> LENGTH: 4
<212> TYPE: PRT
<213> ORGANISM: Artificial Sequence
<220> FEATURE:
<223> OTHER INFORMATION: Description of Artificial Sequence: recombinant

<400> SEQUENCE: 11

Tyr Pro Phe Pro
 1

<210> SEQ ID NO 12
<211> LENGTH: 5
<212> TYPE: PRT
<213> ORGANISM: Artificial Sequence
<220> FEATURE:
<223> OTHER INFORMATION: Description of Artificial Sequence: recombinant

<400> SEQUENCE: 12

Tyr Ala Gly Phe Leu
 1               5

<210> SEQ ID NO 13
<211> LENGTH: 6
<212> TYPE: PRT
<213> ORGANISM: Artificial Sequence
<220> FEATURE:
<223> OTHER INFORMATION: Description of Artificial Sequence: recombinant

<400> SEQUENCE: 13

Tyr Ser Gly Phe Leu Thr
 1               5

<210> SEQ ID NO 14
<211> LENGTH: 3
<212> TYPE: PRT
<213> ORGANISM: Artificial Sequence
<220> FEATURE:
<223> OTHER INFORMATION: Description of Artificial Sequence: recombinant

<400> SEQUENCE: 14

Tyr Gly Phe
 1

<210> SEQ ID NO 15
```

```
<211> LENGTH: 7
<212> TYPE: PRT
<213> ORGANISM: Artificial Sequence
<220> FEATURE:
<223> OTHER INFORMATION: Description of Artificial Sequence: recombinant

<400> SEQUENCE: 15

Tyr Ala Phe Asp Val Val Gly
 1               5

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: recombinant

<400> SEQUENCE: 16

Tyr Ala Phe Glu Val Val Gly
 1               5

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: recombinant

<400> SEQUENCE: 17

Tyr Met Phe His Leu Met Asp
 1               5

<210> SEQ ID NO 18
<211> LENGTH: 17
<212> TYPE: PRT
<213> ORGANISM: Artificial Sequence
<220> FEATURE:
<223> OTHER INFORMATION: Description of Artificial Sequence: recombinant

<400> SEQUENCE: 18

Tyr Gly Gly Phe Leu Arg Arg Ile Arg Pro Lys Leu Lys Trp Asp Asn
 1               5                  10                  15

Gln

<210> SEQ ID NO 19
<211> LENGTH: 8
<212> TYPE: PRT
<213> ORGANISM: Artificial Sequence
<220> FEATURE:
<223> OTHER INFORMATION: Description of Artificial Sequence: recombinant

<400> SEQUENCE: 19

Tyr Gly Gly Phe Leu Arg Arg Ile
 1               5

<210> SEQ ID NO 20
<211> LENGTH: 13
<212> TYPE: PRT
<213> ORGANISM: Artificial Sequence
<220> FEATURE:
<223> OTHER INFORMATION: Description of Artificial Sequence: recombinant

<400> SEQUENCE: 20

Tyr Gly Gly Phe Leu Arg Arg Ile Arg Pro Lys Leu Lys
 1               5                  10
```

```
<210> SEQ ID NO 21
<211> LENGTH: 11
<212> TYPE: PRT
<213> ORGANISM: Artificial Sequence
<220> FEATURE:
<223> OTHER INFORMATION: Description of Artificial Sequence: recombinant

<400> SEQUENCE: 21

Arg Pro Lys Pro Gln Gln Phe Phe Gly Leu Met
 1               5                  10

<210> SEQ ID NO 22
<211> LENGTH: 12
<212> TYPE: PRT
<213> ORGANISM: Artificial Sequence
<220> FEATURE:
<223> OTHER INFORMATION: Description of Artificial Sequence: recombinant

<400> SEQUENCE: 22

Arg Pro Lys Pro Gln Gln Phe Phe Gly Leu Met Gly
 1               5                  10

<210> SEQ ID NO 23
<211> LENGTH: 13
<212> TYPE: PRT
<213> ORGANISM: Artificial Sequence
<220> FEATURE:
<223> OTHER INFORMATION: Description of Artificial Sequence: recombinant

<400> SEQUENCE: 23

Arg Pro Lys Pro Gln Gln Phe Phe Gly Leu Met Gly Lys
 1               5                  10

<210> SEQ ID NO 24
<211> LENGTH: 14
<212> TYPE: PRT
<213> ORGANISM: Artificial Sequence
<220> FEATURE:
<223> OTHER INFORMATION: Description of Artificial Sequence: recombinant

<400> SEQUENCE: 24

Arg Pro Lys Pro Gln Gln Phe Phe Gly Leu Met Gly Lys Arg
 1               5                  10

<210> SEQ ID NO 25
<211> LENGTH: 12
<212> TYPE: PRT
<213> ORGANISM: Artificial Sequence
<220> FEATURE:
<223> OTHER INFORMATION: Description of Artificial Sequence: recombinant

<400> SEQUENCE: 25

Arg Pro Lys Pro Gln Gln Phe Phe Gly Leu Met Gly
 1               5                  10

<210> SEQ ID NO 26
<211> LENGTH: 13
<212> TYPE: PRT
<213> ORGANISM: Artificial Sequence
<220> FEATURE:
<223> OTHER INFORMATION: Description of Artificial Sequence: recombinant

<400> SEQUENCE: 26

Arg Pro Lys Pro Gln Gln Phe Phe Gly Leu Met Gly Lys
 1               5                  10

<210> SEQ ID NO 27
```

```
<211> LENGTH: 14
<212> TYPE: PRT
<213> ORGANISM: Artificial Sequence
<220> FEATURE:
<223> OTHER INFORMATION: Description of Artificial Sequence: recombinant

<400> SEQUENCE: 27

Arg Pro Lys Pro Gln Gln Phe Phe Gly Leu Met Gly Lys Arg
 1               5                  10

<210> SEQ ID NO 28
<211> LENGTH: 12
<212> TYPE: PRT
<213> ORGANISM: Artificial Sequence
<220> FEATURE:
<223> OTHER INFORMATION: Description of Artificial Sequence: recombinant

<400> SEQUENCE: 28

Arg Pro Lys Pro Gln Gln Phe Phe Gly Leu Met Gly
 1               5                  10

<210> SEQ ID NO 29
<211> LENGTH: 13
<212> TYPE: PRT
<213> ORGANISM: Artificial Sequence
<220> FEATURE:
<223> OTHER INFORMATION: Description of Artificial Sequence: recombinant

<400> SEQUENCE: 29

Arg Pro Lys Pro Gln Gln Phe Phe Gly Leu Met Gly Lys
 1               5                  10

<210> SEQ ID NO 30
<211> LENGTH: 14
<212> TYPE: PRT
<213> ORGANISM: Artificial Sequence
<220> FEATURE:
<223> OTHER INFORMATION: Description of Artificial Sequence: recombinant

<400> SEQUENCE: 30

Arg Pro Lys Pro Gln Gln Phe Phe Gly Leu Met Gly Lys Arg
 1               5                  10

<210> SEQ ID NO 31
<211> LENGTH: 4
<212> TYPE: PRT
<213> ORGANISM: Artificial Sequence
<220> FEATURE:
<223> OTHER INFORMATION: Description of Artificial Sequence: recombinant

<400> SEQUENCE: 31

Arg Pro Lys Pro
 1

<210> SEQ ID NO 32
<211> LENGTH: 7
<212> TYPE: PRT
<213> ORGANISM: Artificial Sequence
<220> FEATURE:
<223> OTHER INFORMATION: Description of Artificial Sequence: recombinant

<400> SEQUENCE: 32

Arg Pro Lys Pro Gln Gln Phe
 1               5

<210> SEQ ID NO 33
<211> LENGTH: 9
```

```
<212> TYPE: PRT
<213> ORGANISM: Artificial Sequence
<220> FEATURE:
<223> OTHER INFORMATION: Description of Artificial Sequence: recombinant

<400> SEQUENCE: 33

Arg Pro Lys Pro Gln Gln Phe Phe Gly
  1               5

<210> SEQ ID NO 34
<211> LENGTH: 11
<212> TYPE: PRT
<213> ORGANISM: Artificial Sequence
<220> FEATURE:
<223> OTHER INFORMATION: Description of Artificial Sequence: recombinant

<400> SEQUENCE: 34

Arg Pro Lys Pro Gln Gln Phe Phe Trp Leu Met
  1               5                  10

<210> SEQ ID NO 35
<211> LENGTH: 12
<212> TYPE: PRT
<213> ORGANISM: Artificial Sequence
<220> FEATURE:
<223> OTHER INFORMATION: Description of Artificial Sequence: recombinant

<400> SEQUENCE: 35

Arg Pro Lys Pro Gln Gln Phe Phe Trp Leu Met Gly
  1               5                  10

<210> SEQ ID NO 36
<211> LENGTH: 11
<212> TYPE: PRT
<213> ORGANISM: Artificial Sequence
<220> FEATURE:
<223> OTHER INFORMATION: Description of Artificial Sequence: recombinant

<400> SEQUENCE: 36

Arg Pro Lys Pro Gln Gln Trp Phe Trp Leu Met
  1               5                  10

<210> SEQ ID NO 37
<211> LENGTH: 12
<212> TYPE: PRT
<213> ORGANISM: Artificial Sequence
<220> FEATURE:
<223> OTHER INFORMATION: Description of Artificial Sequence: recombinant

<400> SEQUENCE: 37

Arg Pro Lys Pro Gln Gln Trp Phe Trp Leu Met Gly
  1               5                  10

<210> SEQ ID NO 38
<211> LENGTH: 11
<212> TYPE: PRT
<213> ORGANISM: Artificial Sequence
<220> FEATURE:
<223> OTHER INFORMATION: Description of Artificial Sequence: recombinant

<400> SEQUENCE: 38

Arg Pro Cys Pro Gln Cys Phe Tyr Gly Pro Met
  1               5                  10

<210> SEQ ID NO 39
<211> LENGTH: 6
<212> TYPE: PRT
```

-continued

```
<213> ORGANISM: Artificial Sequence
<220> FEATURE:
<223> OTHER INFORMATION: Description of Artificial Sequence: recombinant

<400> SEQUENCE: 39

Glu Phe Phe Gly Leu Met
 1               5

<210> SEQ ID NO 40
<211> LENGTH: 6
<212> TYPE: PRT
<213> ORGANISM: Artificial Sequence
<220> FEATURE:
<223> OTHER INFORMATION: Description of Artificial Sequence: recombinant

<400> SEQUENCE: 40

Glu Phe Phe Pro Leu Met
 1               5

<210> SEQ ID NO 41
<211> LENGTH: 6
<212> TYPE: PRT
<213> ORGANISM: Artificial Sequence
<220> FEATURE:
<223> OTHER INFORMATION: Description of Artificial Sequence: recombinant

<400> SEQUENCE: 41

Asp Phe Phe Gly Leu Met
 1               5

<210> SEQ ID NO 42
<211> LENGTH: 7
<212> TYPE: PRT
<213> ORGANISM: Artificial Sequence
<220> FEATURE:
<223> OTHER INFORMATION: Description of Artificial Sequence: recombinant

<400> SEQUENCE: 42

Tyr Pro Phe Phe Gly Leu Met
 1               5

<210> SEQ ID NO 43
<211> LENGTH: 7
<212> TYPE: PRT
<213> ORGANISM: Artificial Sequence
<220> FEATURE:
<223> OTHER INFORMATION: Description of Artificial Sequence: recombinant

<400> SEQUENCE: 43

Tyr Pro Phe Phe Pro Leu Met
 1               5
```